United States Patent
Hoffmockel et al.

(10) Patent No.: US 7,301,055 B2
(45) Date of Patent: Nov. 27, 2007

(54) PROCESS FOR REMOVING METHANOL FROM FORMALDEHYDE-CONTAINING SOLUTIONS

(75) Inventors: Michael Hoffmockel, Niedernhausen (DE); Matthias Göring, Hofheim (DE); Juergen Lingnau, Mainz-Laubenheim (DE); Karl-Friedrich Mück, Wiesbaden (DE)

(73) Assignee: Ticona GmbH (DE)

( * ) Notice: Subject to any disclaimer, the term of this patent is extended or adjusted under 35 U.S.C. 154(b) by 186 days.

(21) Appl. No.: 10/451,469

(22) PCT Filed: Nov. 19, 2001

(86) PCT No.: PCT/EP01/13351

§ 371 (c)(1),
(2), (4) Date: Jul. 22, 2003

(87) PCT Pub. No.: WO02/48082

PCT Pub. Date: Jun. 20, 2002

(65) Prior Publication Data

US 2004/0097762 A1    May 20, 2004

(30) Foreign Application Priority Data

Dec. 15, 2000 (DE) .................. 100 62 814

(51) Int. Cl.
*C07C 45/29* (2006.01)
*C07C 27/26* (2006.01)

(52) U.S. Cl. .................. 568/472; 568/913; 568/918

(58) Field of Classification Search ................ 568/472, 568/913, 918
See application file for complete search history.

(56) References Cited

U.S. PATENT DOCUMENTS

| 3,853,719 A | 12/1974 | Matthias et al. ............... 203/56 |
| 4,348,540 A | 9/1982 | Ferris et al. ................. 568/472 |
| 4,967,014 A * | 10/1990 | Masamoto et al. ......... 568/458 |
| 6,015,875 A | 1/2000 | Smith, Jr. et al. ........... 528/501 |

FOREIGN PATENT DOCUMENTS

| GB | 944785 | 12/1963 |
| WO | 98/55435 | 12/1998 |

OTHER PUBLICATIONS

Kolah, Aspi K., et al, "Acetalization of Formaldehyde with Methanol in Batch and Continuous Reactive Distillation Columns," Chemical Abs. 125:19905h, XP-002189207, (Oct. 14, 1996) & Ind. Eng. Chem. Res. (1996), 25(10), 3707-3720.

Zhou, Wei, et al, "Application of catalytic distillation in the synthesis of methylal," Chemical Abs. 132:13270g, XP-002189208, (Jan. 10, 2000) & Gongye Cuihua (1998), 6(1), 35-39.

* cited by examiner

*Primary Examiner*—Sikarl A. Witherspoon
(74) *Attorney, Agent, or Firm*—Connolly Bove Lodge & Hutz LLP

(57) ABSTRACT

Process for removing methanol from formaldehyde-containing solutions. The present invention relates to a process for removing methanol from formaldehyde-containing solutions, with methanol being converted into formaldehyde dimethyl acetal by reactive distillation in the presence of an acidic fixed-bed catalyst, and the resultant mixture comprising methanol, formaldehyde dimethyl acetal and possibly other impurities being distilled off.

16 Claims, 1 Drawing Sheet

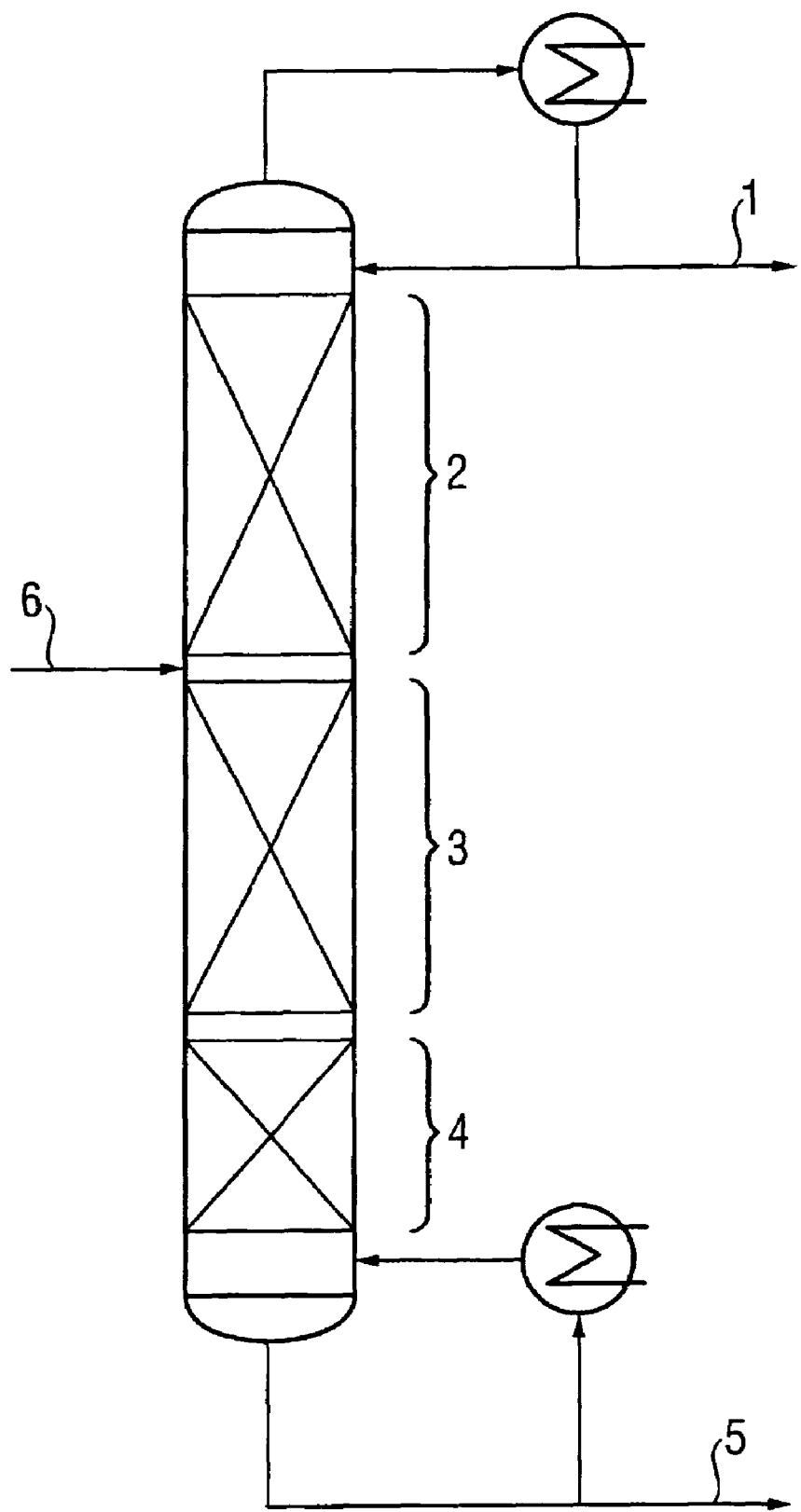

PROCESS FOR REMOVING METHANOL FROM FORMALDEHYDE-CONTAINING SOLUTIONS

RELATED APPLICATIONS

This application is the national stage of PCT/EP01/13351 filed Nov. 19, 2001, and published as WO 02/48082 on Jun. 20, 2002.

This application relates to German patent application number 10062814.1. This related patent application and all references cited herein are incorporated by reference in its entireties for all useful purposes.

The present invention relates to a process for removing impurities, in particular methanol, from formaldehyde-containing solutions, in which methanol is reacted with formaldehyde to give formaldehyde dimethyl acetal and distilled off.

Aqueous formaldehyde generally contains fractions of methanol and other impurities. These may have been added as stabilizer or may be unreacted starting material from the production process or by-products from the production process. If these impurities interfere with the use of the formaldehyde, they must be removed. CH 688041 describes a process for the preparation of formaldehyde dimethyl acetal by reactive distillation of formaldehyde and methanol in the presence of an acidic ion exchanger.

DE 2201865 describes the reduction in the methanol content of an aqueous formaldehyde solution by addition of bodied oils which comprise mixtures of alcohols and dialkyl ethers, each having more than seven carbon atoms. In this process, however, traces of the oil remain in the formaldehyde and may in turn themselves be interfering on subsequent use of the formaldehyde. U.S. Pat. No. 4,348,540 describes the removal of methanol by expulsion with a stream of inert gas. In this process, however, from one to six percent by weight of methanol remain in the formaldehyde.

The object of the present invention was therefore to find a process in which the content of low-boiling impurities can be reduced to less than 6% by weight, preferably less than 5% by weight, in particular less than 3% by weight, of impurities and the methanol content can be reduced to less than one percent by weight in which no assistants need to be added. This object is achieved by a process for removing methanol from formaldehyde-containing solutions in which methanol is converted into formaldehyde dimethyl acetal by reactive distillation in the presence of an acidic fixed-bed catalyst, and the resultant mixture comprising methanol, formaldehyde dimethyl acetal and possibly other impurities is distilled off. Surprisingly, it has been found that on use of the process according to the invention, more methanol is found in the distillate than would have been expected in the case of azeotropic distillation.

The purified formaldehyde solution remains at the bottom of the column, while the impurities are distilled off and are found in the distillate, which comprises, in particular, a formaldehyde dimethyl acetal/methanol mixture.

In the process according to the invention, the formaldehyde-containing solution is advantageously metered continuously into a reactive distillation column in whose reaction zone methanol and formaldehyde react to give formaldehyde methyl acetal, and the formaldehyde dimethyl acetal is distilled off at the top of the column as a mixture with methanol and possibly further impurities. This process enables, in particular, the volatility of the methanol to be increased and thus the column still, which contains formaldehyde and the solvent, can be substantially freed from methanol.

The distillation for separation of the mixture is advantageously carried out as a fractional distillation in a plurality of steps.

The formaldehyde-containing solution is generally an aqueous formaldehyde solution. The formaldehyde-containing solution comprises from 10% by weight to 80% by weight, advantageously from 10 to 63% by weight, mostly more than 15% by weight, particularly advantageously from 17% by weight to 37% by weight, in particular from 17 to 22% by weight, of formaldehyde. Besides methanol, the formaldehyde-containing solution may also contain other impurities depending on its origin, in particular on the production process, such as, for example, 2,4,6-trioxaheptane, formic acid, methyl formate, trioxane, aldehydes, acrolein, glyoxal, propionaldehyde, acetaldehyde, ketones, acetone, 2-butanone, dimethyl ether or esters, either individually or as a mixture with other compounds mentioned above. Methanol is usually present in the formaldehyde-containing solutions in an amount of from 1% by weight to 20% by weight, advantageously less than 10% by weight, in particular less than 5% by weight.

In a particularly advantageous embodiment of the invention, the molar ratio between the concentrations of formaldehyde and methanol is at least 3.

The fixed-bed catalyst used can advantageously be a polymeric ion exchanger resin, i.e. a polymer containing acidic functional groups, or a zeolite. It is particularly advantageous to use a crosslinked polystyrene containing sulfonic acid groups. The process according to the invention is advantageously carried out downstream of a process carried out beforehand for the preparation of formaldehyde. In this process, formaldehyde is usually prepared by oxidation or oxydehydrogenation of methanol. In particularly preferred embodiment of the present process, the distillate is fed to a further use. The formaldehyde dimethyl acetal/methanol mixture is very particularly preferably fed as starting material to a process for the preparation of formaldehyde carried out upstream of the purification processes according to the invention. In a further advantageous embodiment of the present invention, the formaldehyde purified by the process according to the invention is subjected to a downstream process for the preparation of trioxane or polyoxymethylene. The present invention therefore also relates to a process for the preparation of formaldehyde, in which formaldehyde is prepared by oxidation or oxydehydrogenation of methanol, the formaldehyde is purified, with methanol being converted into formaldehyde dimethyl acetal by reactive distillation in the presence of an acidic fixed-bed catalyst, and the resultant mixture comprising methanol, formaldehyde dimethyl acetal and possibly other impurities is distilled off.

The invention furthermore relates to a process for the preparation of trioxane in which formaldehyde is prepared by oxidation or oxydehydrogenation of methanol, the formaldehyde is purified, with methanol being converted into formaldehyde dimethyl acetal by reactive distillation in the presence of an acidic fixed-bed catalyst, and the resultant mixture comprising methanol, formaldehyde dimethyl acetal and possibly other impurities being distilled off, the formaldehyde obtained in this way is used for the preparation of trioxane.

A BRIEF DESCRIPTION OF THE FIGURE

The figure illustrates an example of an apparatus for carrying of the process according to the invention.

Details on the preparation of trioxane are known to the person skilled in the art and are described, for example, in Kirk-Othmer, Encyclopedia of Chemical Technology, 2$^{nd}$ Edn., Volume 10, pp. 83 and 89, Interscience, New York, 1963-1972, which is incorporated herein by way of reference.

The invention likewise relates to a process for the preparation of polyoxymethylene in which
formaldehyde is prepared by oxidation or oxydehydrogenation of methanol,
the formaldehyde is purified, with methanol being converted into formaldehyde dimethyl acetal by reactive distillation in the presence of an acidic fixed-bed catalyst, and the resultant mixture comprising methanol, formaldehyde dimethyl acetal and possibly other impurities being distilled off,
the formaldehyde is converted into anhydrous formaldehyde,
the formaldehyde is polymerized,
the end groups of the polymer prepared in this way are saturated (capped), and,
if desired, the polymer is homogenized in the melt and/or provided with suitable additives.

The preparation of polyoxymethylene is known to the person skilled in the art and is described, for example, in Ullmann's Encyclopedia of Industrial Chemistry, Volume 21, 5$^{th}$ Edn., Weinheim, 1982, and the literature cited therein, which is expressly incorporated herein by way of reference.

The present invention furthermore relates to a process for the preparation of polyoxymethylene copolymers in which
formaldehyde is prepared by oxidation or oxydehydrogenation of methanol,
the formaldehyde is purified, with methanol being converted into formaldehyde dimethyl acetal by reactive distillation in the presence of an acidic fixed-bed catalyst, and the resultant mixture comprising methanol, formaldehyde dimethyl acetal and possibly other impurities being distilled off,
the formaldehyde obtained in this way is used for the preparation of trioxane,
the trioxane is purified if necessary,
the trioxane is copolymerized with cyclic ethers or cyclic acetals,
any unstable end groups are removed, and
the polymer prepared in this way is, if desired, homogenized in the melt and/or provided with suitable additives.

The invention furthermore relates to a process for the preparation of polyoxymethylene copolymers in which
formaldehyde is prepared by oxidation of methanol,
the formaldehyde is purified, with methanol being converted into formaldehyde dimethyl acetal by reactive distillation in the presence of an acidic fixed-bed catalyst, and the resultant mixture comprising methanol, formaldehyde dimethyl acetal and possibly other impurities being distilled off,
the formaldehyde is converted into anhydrous formaldehyde,
the formaldehyde is copolymerized with cyclic ethers or cyclic acetals,
any unstable end groups are removed, and
the polymer is, if desired, homogenized in the melt and/or provided with suitable additives.

The preparation of polyoxymethylene copolymers is known to the person skilled in the art and is described, for example, in Ullmann's Encyclopedia of Industrial Chemistry, Vol. 21, 5$^{th}$ Edn., Weinheim, 1992, and the literature cited therein, which is expressly incorporated herein by way of reference.

An advantageous apparatus for carrying out this process is shown in FIG. 1 and advantageously has a distillate outlet 1, stripping section 2, rectifying section 4, a reaction zone 3 and a product outlet 5 and a feed for the formaldehyde-containing solution 6. If the apparatus used is a distillation column, the reaction zone can also be located outside the column. In this case, the return is taken from a tray of the column, passed over an acidic catalyst fixed bed and subsequently fed back below said tray of the column. This arrangement can also be employed a number of times at successive column trays.

In the preferred embodiment, however, the reaction zone is integrated into the column. The reaction zone is provided with packing elements which fix the acidic fixed-bed catalyst. Particularly suitable packing elements are, for example, Sulzer Katapak-S® elements, which are fitted with an acidic ion exchanger, such as, for example, Amberlyst 15®.

The stripping and rectification sections employed are preferably columns, in particular surface rectifiers, such as packed columns or tray columns, where tray columns have a large retention capacity and packed columns have a large specific surface area. Particularly preferred columns are bubble-tray columns, trickle columns, columns containing packing and columns containing ordered packing. In order to achieve the lowest possible column height with high throughputs, preference is given to columns having internals which provide the largest possible exchange area, for example with structured packing.

It is intended to clarify the present invention to the person skilled in the art with reference to the following examples without restricting the scope of protection.

EXAMPLES

The DN50 column was constructed in accordance with FIG. 1. The Katapak® elements (3), which were installed in the two reactive shots, each contained 150 g (dry weight) of Amberlyst-15® as acidic ion exchanger and were employed in a length of 2 m. The capacity of the catalyst is about 4.75 meq/g. 1 m Sulzer BX were employed in each of the stripping section and the rectification section. A total of six experiments were carried out at atmospheric pressure with the set-up shown in FIG. 1. An overview of the experiments carried out is given in Table 1. The magnitude of the feed streams, the distillate stream and the bottom-product stream were determined gravimetrically. The temperatures and pressure at the top and bottom of the column and the differential pressure were recorded via a process control system. After the temperature profile had stabilized, which was the case in from approximately 2 to 4 hours, depending on the size of the feed stream, and was then stable for at least twice the hydrodynamic residence time, samples were taken from the liquid phase.

Analysis was carried out by gas chromatography and titration. The results of the analyses are listed in Tables 2-7. In all experiments, the methanol content in the bottom product was significantly reduced with that in the feed. In experiments 3 and 6, 0.08% of methanol was achieved in the bottom product, which corresponds to removal of 97.8% of the methanol.

TABLE 1

Overview of the experiment carried out

| Experiment number | Feed [kg/h] | Heating power [W] | Condenser power [W] | Distillate [g/h] | Reflux ratio | Methanol removal |
|---|---|---|---|---|---|---|
| C1 | 3.945 | 888 | 332 | 57.3 | ca. 75 | 74.7% |
| C2 | 3.885 | 888 | 336 | 171.5 | ca. 25 | 80.5% |
| C3 | 4.007 | 1203 | 663 | 109.7 | ca. 40 | 97.8% |
| C4 | 3.984 | 1203 | 630 | 86.9 | 80 | 80.5% |
| C5 | 2.010 | 753 | 310 | 33.0 | 20 | 89.4% |
| C6 | 2.025 | 753 | 313 | 26.3 | 25 | 97.9% |

TABLE 2

Experiment 1

| Composition | Feed | Bottom product | Distillate |
|---|---|---|---|
| Water | 72.13% | 75.10% | 12.70% |
| Formaldehyde | 19.39% | 20.22% | 0.97% |
| Methanol | 3.28% | 0.83% | 38.25% |
| Formaldehyde dimethyl acetal | 0.10% | 0.00% | 28.90% |
| 2,4,6-trioxaheptane | 0.10% | 0.00% | 16.30% |
| Trioxane | 4.72% | 3.57% | 1.12% |
| Formic acid | 0.28% | 0.28% | 0.44% |
| Methyl formate | 0.00% | 0.00% | 1.32% |
| Total | 100.00% | 100.00% | 100.00% |

TABLE 3

Experiment 2

| Composition | Feed | Bottom product | Distillate |
|---|---|---|---|
| Water | 70.27% | 77.75% | 10.55% |
| Formaldehyde | 20.39% | 20.30% | 3.51% |
| Methanol | 3.64% | 0.71% | 26.24% |
| Formaldehyde dimethyl acetal | 0.12% | 0.00% | 27.62% |
| Dioxy ether | 0.10% | 0.00% | 5.01% |
| Trioxane | 5.11% | 0.80% | 24.73% |
| Formic acid | 0.37% | 0.44% | 0.68% |
| Methyl formate | 0.00% | 0.00% | 1.66% |
| Total | 100.00% | 100.00% | 100.00% |

TABLE 4

Experiment 3

| Composition | Feed | Bottom product | Distillate |
|---|---|---|---|
| Water | 70.27% | 78.16% | 13.57% |
| Formaldehyde | 20.39% | 20.45% | 2.40% |
| Methanol | 3.64% | 0.08% | 45.41% |
| Formaldehyde dimethyl acetal | 0.12% | 0.00% | 23.54% |
| Dioxy ether | 0.10% | 0.00% | 6.72% |
| Trioxane | 5.11% | 0.88% | 6.00% |
| Formic acid | 0.37% | 0.43% | 0.78% |
| Methyl formate | 0.00% | 0.00% | 1.58% |
| Total | 100.00% | 100.00% | 100.00% |

TABLE 5

Experiment 4

| Composition | Feed | Bottom product | Distillate |
|---|---|---|---|
| Water | 70.27% | 75.18% | 9.50% |
| Formaldehyde | 20.39% | 19.75% | 2.72% |
| Methanol | 3.64% | 0.71% | 39.64% |
| Formaldehyde dimethyl acetal | 0.12% | 0.00% | 34.54% |
| 2,4,6-trioxaheptane | 0.10% | 0.01% | 6.77% |
| Trioxane | 5.11% | 3.29% | 4.05% |
| Formic acid | 0.37% | 1.06% | 0.73% |
| Methyl formate | 0.00% | 0.00% | 2.05% |
| Total | 100.00% | 100.00% | 100.00% |

TABLE 6

Experiment 5

| Composition | Feed | Bottom product | Distillate |
|---|---|---|---|
| Water | 71.06% | 76.85% | 13.33% |
| Formaldehyde | 20.08% | 20.99% | 0.17% |
| Methanol | 3.88% | 0.41% | 48.85% |
| Formaldehyde dimethyl acetal | 0.11% | 0.00% | 31.65% |
| 2,4,6-trioxaheptane | 0.08% | 0.00% | 3.01% |
| Trioxane | 4.48% | 1.52% | 0.17% |
| Formic acid | 0.31% | 0.23% | 0.58% |
| Methyl formate | 0.00% | 0.00% | 2.24% |
| Total | 100.00% | 100.00% | 100.00% |

TABLE 7

Experiment 6

| Composition | Feed | Bottom product | Distillate |
|---|---|---|---|
| Water | 71.06% | 76.34% | 0.44% |
| Formaldehyde | 20.08% | 21.42% | 0.11% |
| Methanol | 3.88% | 0.08% | 34.12% |
| Formaldehyde dimethyl acetal | 0.11% | 0.00% | 55.67% |
| 2,4,6-trioxaheptane | 0.08% | 0.00% | 4.17% |
| Trioxane | 4.48% | 1.94% | 0.08% |
| Formic acid | 0.31% | 0.22% | 0.96% |
| Methyl formate | 0.00% | 0.00% | 4.45% |
| Total | 100.00% | 100.00% | 100.00% |

The invention claimed is:

1. A process for removing methanol from formaldehyde-containing solutions, in which methanol is converted into formaldehyde dimethyl acetal by reactive distillation in the presence of an acidic fixed-bed catalyst, and the resultant mixture comprising methanol, formaldehyde dimethyl acetal and possibly other impurities is distilled off and the molar ratio between the concentrations of formaldehyde and methanol is at least 3 and wherein the methanol content is least than 1 percent by weight.

2. A process for the preparation of formaldehyde, in which formaldehyde is prepared by oxidation or oxydehydrogenation of methanol, and the formaldehyde is purified, with methanol being converted into formaldehyde dimethyl acetal by reactive distillation in the presence of an acidic fixed-bed catalyst, and the resultant mixture comprising methanol, formaldehyde dimethyl acetal and possibly other impurities being distilled off and the molar ratio between the concentrations of formaldehyde and methanol is at least 3 and wherein the methanol content is less than 1 percent by weight.

3. The process as claimed in claim 1, wherein the distillation of the mixture is carried out as a fractional distillation in a plurality of steps.

4. The process as claimed in claim 1, wherein the acidic fixed-bed catalyst employed is an acidic ion exchanger.

5. The process as claimed in claim 1, wherein the acidic fixed-bed catalyst employed is a crosslinked polystyrene containing sulfonic acid groups.

6. The process as claimed in claim 1, wherein the formaldehyde-containing solution is a solution of formaldehyde in water.

7. The process as claimed in claim 1, wherein the formaldehyde-containing solution comprises from 10 to 80% by weight of formaldehyde.

8. The process as claimed in claim 1, wherein the formaldehyde-containing solution comprises from 1 to 20% by weight of methanol.

9. The process as claimed in claim 1, wherein the formaldehyde-containing solution comprises less than 5% by weight of methanol.

10. The process as claimed in claim 1, wherein the mixture comprising methanol and formaldehyde dimethyl acetal is fed to a formaldehyde preparation process upstream of the process for removing methanol.

11. The process as claimed in claim 1, wherein low boiling impurities are present in an amount to less than 6% by weight.

12. The process as claimed in claim 1, wherein low boiling impurities are present in an amount to less than 5% by weight.

13. The process as claimed in claim 1, wherein low boiling impurities are present in an amount to less than 3% by weight.

14. The process as claimed in claim 2, wherein low boiling impurities are present in an amount to less than 6% by weight.

15. The process as claimed in claim 2, wherein low boiling impurities are present in an amount to less than 5% by weight.

16. The process as claimed in claim 2, wherein low boiling impurities are present in an amount to less than 3% by weight.

* * * * *